United States Patent
Tamura et al.

(10) Patent No.: US 8,547,547 B2
(45) Date of Patent: Oct. 1, 2013

(54) OPTICAL SURFACE DEFECT INSPECTION APPARATUS AND OPTICAL SURFACE DEFECT INSPECTION METHOD

(75) Inventors: Shintaro Tamura, Kamisato (JP); Masanori Fukawa, Kamisato (JP); Ayumu Ishihara, Kamisato (JP); Kenichi Shitara, Kamisato (JP); Hiroshi Nakajima, Chigasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 110 days.

(21) Appl. No.: 13/213,116

(22) Filed: Aug. 19, 2011

(65) Prior Publication Data
US 2012/0075625 A1 Mar. 29, 2012

(30) Foreign Application Priority Data
Sep. 24, 2010 (JP) .................................. 2010-213731

(51) Int. Cl.
*G01N 21/00* (2006.01)
(52) U.S. Cl.
CPC ....................................... *G01N 21/00* (2013.01)
USPC .................................... 356/237.5; 356/237.2
(58) Field of Classification Search
CPC ..................................................... G01N 21/00
USPC .......................................... 356/237.1–237.5
See application file for complete search history.

(56) References Cited

U.S. PATENT DOCUMENTS

| RE31,815 E | * | 1/1985 | Alfano | 600/477 |
| 5,798,831 A | * | 8/1998 | Hagiwara | 356/237.2 |
| 2002/0005947 A1 | * | 1/2002 | Golberg et al. | 356/237.2 |
| 2004/0095571 A1 | * | 5/2004 | Bourely et al. | 356/237.1 |

FOREIGN PATENT DOCUMENTS

JP 2-61542 3/1990

\* cited by examiner

*Primary Examiner* — Michael P Stafira
(74) *Attorney, Agent, or Firm* — Antonelli, Terry, Stout & Kraus, LLP.

(57) ABSTRACT

The present invention is to provide an optical surface defect inspection apparatus or an optical surface defect inspection method that can improve a signal-to-noise ratio according to a multi-segmented cell method without performing autofocus operations, and can implement highly sensitive inspection. The present invention is an optical surface defect inspection apparatus or an optical surface defect inspection method in which an inspection beam is applied onto a test subject, an image of a scattered light from the surface of the test subject is formed on a photo-detector, and a defect on the surface of the test subject is inspected based on an output from the photo-detector. The photo-detector has an optical fiber bundle. One end thereof forms a circular light receiving surface to receive the scattered light. The other end thereof is connected to a plurality of light receiving devices. The optical fiber bundle is divided into a plurality of fan-shaped cells in the light receiving surface, and connected to the light emitting devices in units of the cells for performing the inspection based on the outputs of the plurality of cells.

8 Claims, 5 Drawing Sheets

OPTICAL SURFACE DEFECT INSPECTION APPARATUS AND OPTICAL SURFACE DEFECT INSPECTION METHOD

BACKGROUND OF THE INVENTION

1. Field of the Invention

The present invention relates to an optical surface defect inspection apparatus and an optical surface defect inspection method, and more particularly to an optical surface defect inspection apparatus and an optical surface defect inspection method preferable for use in detecting line-shaped micro defects (scratches) produced on the surface of a test subject.

2. Description of the Related Art

Optical surface defect inspection apparatuses for use in detecting micro defects on the surface of a test subject such as a magnetic disk and an IC wafer are demanded to perform high speed inspection that can meet a 100-percent inspection of the entire surface of all test subjects as well as highly sensitive inspection (detection of micro defects having a width of about a few tens nanometers and a depth of about a few nanometers). Line-shaped micro defects (scratches) considerably damage products particularly, and it is essential to inspect these defects. Generally for highly sensitive defect detection, such a method is adopted that a high intensity micro spot is applied to the surface and the micro spot is scanned over the surface for detecting a scattered light from a defect on the surface highly sensitively. It is necessary to coarsen scan pitches for quick completion of overall scanning in order to perform high speed inspection. In this case, however, the size of an applied spot is needed to sufficiently cover at least the scan pitch. However, there is a dilemma that an increased spot size reduces spot intensity and decreases detection sensitivity.

For a method of performing a highly sensitive surface defect inspection at high speed (Japanese Patent Application Laid-Open Publication No. H02-061542), there is a method that a bundle fiber is formed in a multi-segmented cell structure in which the bundle fiber is divided into n small segments, the bundle fiber has a scattered light detector disposed in the radial direction of a test subject, an image in a micro visual field on a micro spot applied to the surface of the test subject is formed on the multi-segmented cells, and the level of background noise per cell (noise mainly caused by surface roughness) is made 1/n. Moreover, in the method described in Japanese Patent Application Laid-Open Publication No. H02-061542, in order to eliminate position dependence in the radial direction, the individual small segments are arranged uniformly in the radial direction. A defect signal in this case is detected at one place in any cells corresponding to the position of the defect. On the other hand, background noise is reduced by 1/n because the cell area is decreased to 1/n of the entire area. Consequently, the level of a cell signal that detects the defect is not made smaller, whereas only noise becomes 1/n, resulting in an increase in the signal-to-noise ratio n times. Furthermore, since the scan pitch can be widened to the width of n cells of the detection cells, inspection speed is not reduced.

SUMMARY OF THE INVENTION

However, in the case of adopting this method, it is essential to provide the resolution of an optical system that is necessary to form an image in the micro visual field on the multi-segmented cells. For example, in the case where a length of one micrometer on a test subject is made to be matched with one cell of a detector, a necessary numerical aperture of an objective lens is determined from demands for the resolution. However, the numerical aperture is increased to make the depth of focus shallow, and even a slight shift in focus blurs an image on the detection cell surface (an image is formed across a plurality of cells), causing no effect of dividing the cells. In order to avoid this problem, generally in the case of adopting a fine segmented cell method, the distance between the objective lens and the test subject surface is kept constant in high speed scanning by an autofocus function.

However, in the case where the scan rate is increased excessively, autofocus operations cannot physically follow the scan rate.

Thus, it is an object of the present invention to provide an optical surface defect inspection apparatus or an optical surface defect inspection method that can improve a signal-to-noise ratio according to a multi-segmented cell method, and can implement highly sensitive inspection without performing autofocus operations.

In order to achieve the foregoing object, the present invention includes at least features described below.

A first aspect of the present invention is an optical surface defect inspection apparatus or an optical surface defect inspection method including: irradiating an inspection beam onto a test subject; forming an image of a scattered light from a surface of the test subject on a photo-detector; and inspecting a defect on the surface of the test subject based on an output from the photo-detector, wherein: the photo-detector includes an optical fiber bundle having one end thereof forming a circular light receiving surface to receive the scattered light, and the other end thereof connected to a plurality of light receiving devices; and the optical fiber bundle is divided into a plurality of fan-shaped cells in the light receiving surface, and connected to the light emitting devices in units of the fan-shaped cells for performing the inspection based on outputs of the plurality of cells.

Moreover, in a second aspect of the present invention, the number of the cells is an even number, and paired cells provided at positions opposite to each other are connected to the same light receiving device.

Furthermore, in a third aspect of the present invention, the inspection determines that a scratch exists when at least a certain pair of the paired cells among the paired cells receive the scattered light with a significant value as compared with the other paired cells.

In addition, in a fourth aspect of the present invention, the inspection determines that a point-like defect or foreign substance exists when there is no significant difference in a light receiving level of the scattered light between the plurality of cells.

Moreover, in a fifth aspect of the present invention, an irradiating unit has a laser Light source.

Furthermore, in a sixth aspect of the present invention, the test subject is a disk-shaped magnetic disk or IC wafer, and the inspection is performed by two-dimensionally scanning the inspection beam over the surface of the test subject.

According to the present invention, it is possible to provide an optical surface defect inspection apparatus or an optical surface defect inspection method that can improve a signal-to-noise ratio according to a multi-segmented cell method, and can implement highly sensitive inspection without performing autofocus operations.

BRIEF DESCRIPTION OF THE DRAWINGS

The present invention will become fully understood from the detailed description given hereinafter and the accompanying drawings, wherein.

DETAILED DESCRIPTION OF THE PREFERRED EMBODIMENTS

Figure 1:
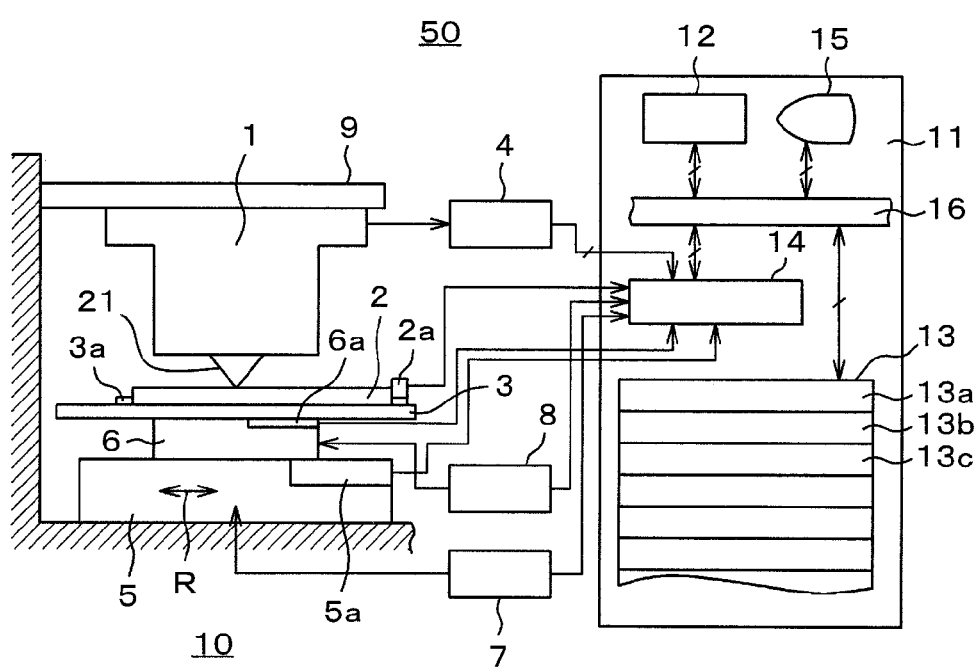
FIG. 1 is a diagram depicting an embodiment of an optical surface defect inspection apparatus.

FIG. 1 is a diagram depicting an embodiment of an optical surface defect inspection apparatus (in the following, simply referred to as an inspection apparatus) 50. The inspection apparatus includes: an inspection optical system 1 that applies an inspection beam onto the surface of a disk-shaped test subject 2, which is a workpiece such as a magnetic disk or IC wafer, and obtains a reflected light; a frame 9 that supports the inspection optical system 1 on the apparatus; a scanning unit 10 that scans the test subject 2 so as to inspect the entire surface of the test subject 2; a pre-processing unit 4 that processes the output of the inspection optical system 1; and a data processing unit 11 that controls the scanning unit 10 and includes a processing unit 12 to receive the output of the pre-processing unit 4 and process data.

First, the configuration of the inspection optical system 1, which is a feature of the embodiment of the present invention, will be described with reference to FIG. 2. The inspection optical system 1 includes: a laser unit (a light source) 20 that applies a laser beam 21 onto the surface of the test subject 2; a scattered light optical system 30 that forms an image of a scattered light 31 in the reflected light from a scratch S on the test subject 2 on a light receiving surface 41m of an optical fiber bundle 41; and a photo-detector 40 having an optical fiber bundle 41 and a plurality of light receiving devices 42 connected to the optical fiber bundle 41.

The scattered light optical system 30 includes an objective lens 32, a mask 34 that blocks a positive reflected light 26 in the reflected light, and an image forming lens 33 that focuses the scattered light 31 with the positive reflected light 26 blocked on a pin hole 35.

Figure 3:
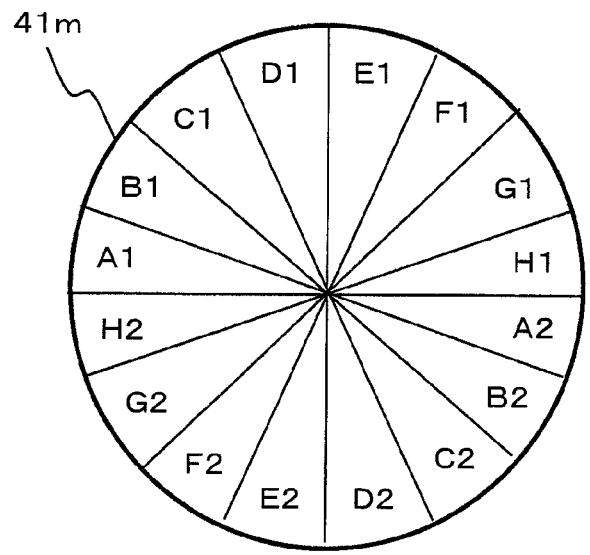
FIG. 3 is a diagram illustrative of the light receiving surface of an optical fiber bundle and a plurality of fan-shaped cells.
Figure 4:
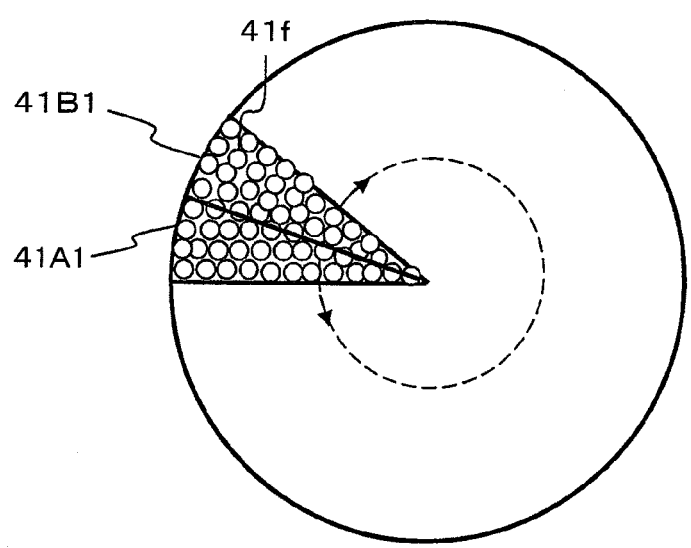
FIG. 4 is a diagram depicting the configuration of cells in which the cells are formed of optical fiber sub-bundles that fine optical fibers are bundled in a fan shape.

As shown in FIG. 3, the light receiving surface 41m of the optical fiber bundle 41 of the photo-detector 40 has a circular shape, and is divided into a plurality of fan-shaped cells A1, B1, C1, and so on. As shown in FIG. 4, the cells have optical fiber sub-bundles 41A1, 41B1, and so on that fine optical fibers 41f are divided into fan shapes. The optical fiber sub-bundle 41A1, 41B1, and so on are connected to the light receiving devices 42A, 42B, and so on in units of bundles. A photo multiplier or the like is used for the light receiving device 42.

Figure 5:
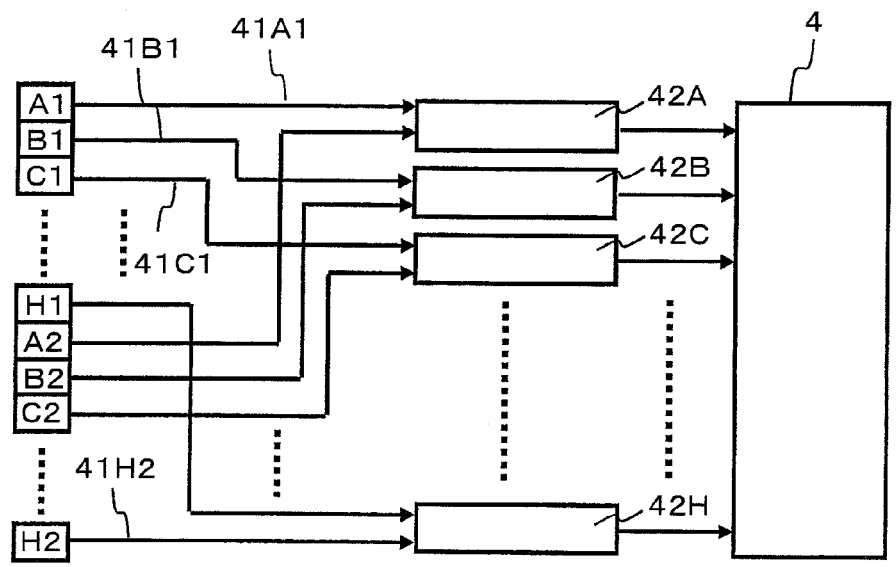
FIG. 5 is a diagram depicting a first embodiment of connections between cells and light receiving devices.

In this embodiment, the light receiving surface 41m is divided into 16 cells A1 to H1 and A2 to H2 as shown in FIG. 4. In a first embodiment, as shown in FIG. 5, the ends of optical fiber sub-bundles of two opposite cells, A1 and A2, for example, are connected to one light receiving device 42A. Similarly, two opposite cells are connected to the corresponding light emitting device 42 in such a way that the cells B1 and B2 are connected to the light receiving device 42B, and the cells C1 and C2 are connected to the light receiving device 42C. In the first embodiment, the number of the light receiving devices 42 for use is a half of the number of cells divided. With this configuration of the photo-detector 40, an image of the scattered light 31 formed on the light receiving surface 41m is guided to the individual light receiving devices 42A to 42H through the cells A1 to H1 and A2 to H2. The outputs of the individual light receiving devices 42A to 42H are amplified and A/D converted at the pre-processing unit 4, and inputted to the data processing unit 11 shown in FIG. 1.

Figure 6:
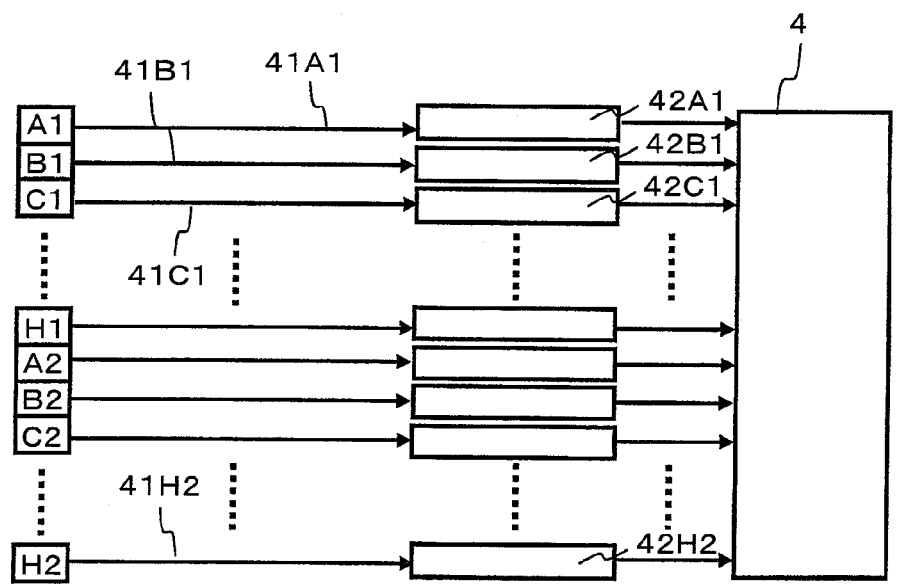
FIG. 6 is a diagram depicting a second embodiment of connections between cells and light receiving devices.

Of course, as shown in a second embodiment in FIG. 6, it is also possible to separately connect the individual cells A1 to H1 and A2 to H2 to light receiving devices 42A1 to 42H1 and 42A2 to 42H2. In this case, the number of cells divided in the light receiving surface may be an odd number.

Next, the operation and effect of the inspection optical system 1 described above will be explained.

Generally, in the case where the surface of the test subject 2 is completely flat like a mirror, the scattered light 31 is rarely produced, and most of the reflected light becomes the positive reflected light 26. On the other hand, in the case where defects such as flaws exist on the surface of the test subject 2, a strong scattered light is produced. This change in the scattered light is captured to detect defects. Moreover, the intensity of scattered light is changed depending on the size or shape of defects.

When defects on the surface of the test subject are scratches and very shallow flaws, a scattered light to be produced is considerably weak, and it is difficult to distinguish between that scattered light and a scattered light that is background noise produced due to surface roughness or the like. Namely, it is difficult to detect the scattered light because the signal-to-noise ratio is low. For these shallow, scratch-like flaws, the embodiment can improve the signal-to-noise ratio and is effective. In the following, an example will be described in which the light receiving surface 41m is divided into 16 cells, which is an even number (2n), with reference to the first embodiment shown in FIGS. 3 and 5.

As described above, when the shape of a defect is a line-shaped scratch, such a characteristic is produced that a scattered light is distributed in the direction at a right angle to the orientation of this scratch. On the other hand, a scattered light (background noise) produced due to the surface roughness of the test subject 2 or the like does not have this characteristic distribution.

Figure 7A:
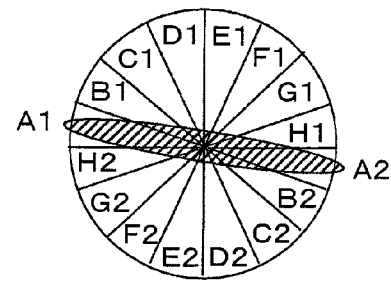
FIGS. 7A to 7C are diagrams schematically depicting the principles of detecting scratches.
Figure 7A:
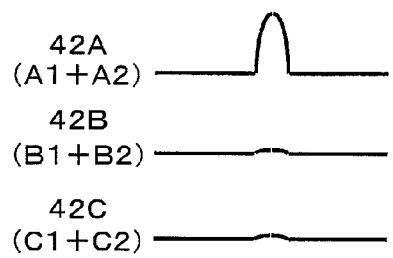
Figure 7B:
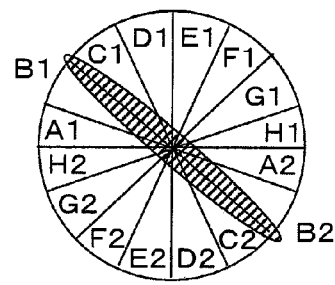
Figure 7B:
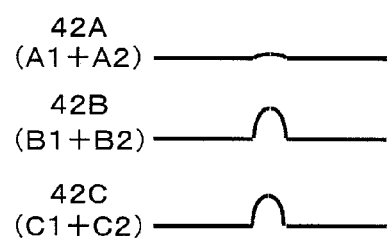
Figure 7C:
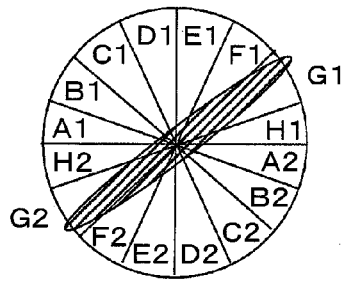
Figure 7C:
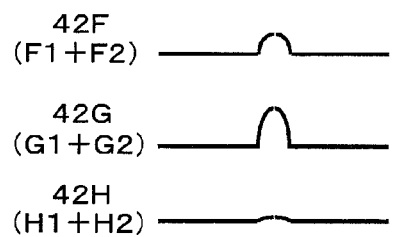

FIGS. 7A to 7C are diagrams schematically depicting the principles of detecting scratch defects. In the upper diagrams shown in FIGS. 7A to 7C, the distribution of a scattered light on the light receiving surface 42m is hatched, and the lower diagrams show output waveforms of the light receiving device 42.

FIG. 7A shows an example in which the cells A1 and A2 detect a strong scattered light, and the light receiving device 42A has a large (a significant) output, whereas the other light receiving devices 42B, 42C, and so on detect almost no light. Namely, this is an example in which the cells A1 and A2 received a scattered light with a significant value more than the other cells did. A scratch in this example exists in the range of an angle covered by the cells A1 and A2, and the adjacent cells B1, B2, C1, and C2 detect almost no light. Thus, it is revealed that a scratch exists at the center between the cell A1 and A2. Therefore, a scratch exists at near a center angle of about 102.5 degrees between the cells A1 and A2 clockwise as a border line between the cells D1 and E1 is a base point.

FIG. 7B shows an example in which the light receiving devices 42B and 42C have a significant output at almost the same level and the other light receiving devices 42A and so on have almost no changes. Similarly considered as the example in FIG. 7A, a scratch exists at a position at an angle of about 145 degrees that is a position on the border between the cells B1 and B2 and the cells C1 and C2.

FIG. 7C shows a more complicated example in which the ratio between the high output wave values of the light receiving device 42F and the light receiving device 42G is 1:2 with a significant value and the output of the adjacent light receiving device 42H is nearly zero. In this case, if a weight is not provided for an angle based on the intensity distribution of the scattered light 31, an angle is divided at a ratio of 1:2, and a scratch exists at a position at an angle of about 40 degrees.

As described above, it is possible to know the angle of a scratch depending on whether a strong scattered light is detected at the position of the light receiving device. However, data shown in FIGS. 7A to 7C is data at one place on the surface of the test subject 2. The entire surface of the test subject 2 is inspected, and adjacent items of data are collected, as described later, so that it is possible to obtain information such as the length including the angle of the scratch S.

In inspection according to the embodiment as described above, since the distribution of a scattered light due to surface roughness or the like is uniform, the background noise of each divided cell is a submultiple of the number of cells divided with respect to the background noise of the entire light receiving surface. For example, in the case where the light receiving surface is divided into 16 cells, the background noise of the cell is 1/16. In the case where two opposite cells are connected to a single light receiving device, the base noise of each individual light receiving device is one-eighth of the total noise. Namely, the signal-to-noise ratio of light receiving sensitivity for a scratch can be improved eight times.

In the discussions above, examples are shown in which scratches are inspected. However, in the case of a point-like defect or foreign substance, the output of a certain cell does not appear strongly more than the other cells like scratches (a cell takes a significant value). In this case, in the optical surface defect inspection apparatus 50 according to this embodiment, it is possible to perform inspection in such a way that if a single cell or a part of or all the optical fiber bundle 41 are regarded as a single detector and a strong output appears in this unit, it is determined that a point-like defect or foreign substance exists.

Figure 2:
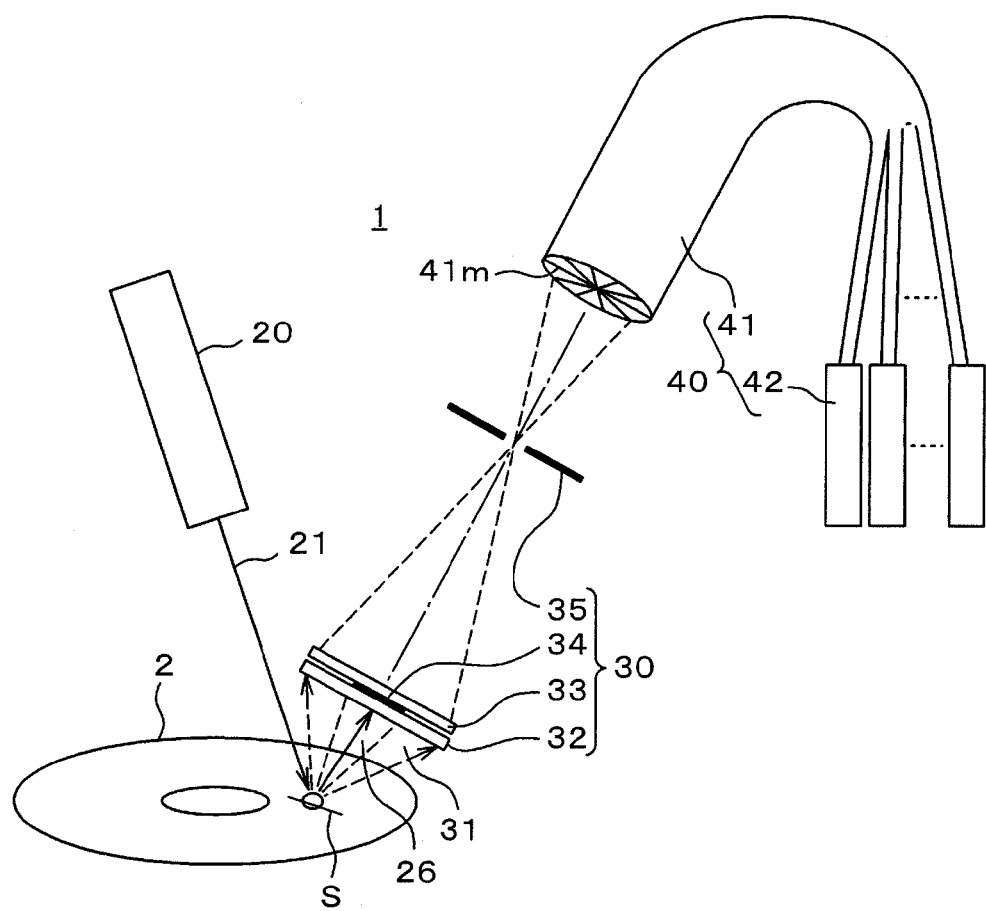
FIG. 2 is a diagram depicting the configuration of an inspection optical system that is a feature of an embodiment of the present invention.

Lastly, a mechanism and operations will be described in which a donut-shaped test subject 2 as shown in FIG. 2 is helically scanned for 100-percent scanning of the entire surface of the test subject. As shown in FIG. 1, a work table 3 is supported on a rectilinear table 5 and a rotation table 6. The rectilinear table 5 linearly moves in the R-direction, and the θ rotation table 6 is provided on this rectilinear table 5. The θ rotation table 6 is provided with an encoder 6a that generates a signal indicating a turning angle, and the rectilinear table 5 is provided with an encoder 5a that indicates a moved position in the R-direction. The signals of the encoders 5a and 6a are sent as scan position signals to the data processing unit 11 (an interface 14). It is noted that 2a denotes a sensor detecting that the test subject 2 is placed on the work table 3. 3a denotes a guide pin that sets the test subject 2 in such a way that the center of the donut-shaped test subject 2 is matched with the rotation center of the θ rotation table 6. 8 denotes a θ direction drive circuit that drives the θ rotation table 6; the rotation direction, rotation velocity, stop position, and the like of the work table 3 are controlled through this drive circuit. 7 denotes an R-direction drive circuit that linearly moves the rectilinear table 5 in the R-direction. These drive circuits are controlled according to control signals from the data processing unit 11.

This mechanism is used to helically scan the test subject 2 according to a constant speed helical scanning program 13b stored in a storage unit 13. More specifically, the test subject 2 is placed in such a way that the center of the test subject 2 is matched with the rotation center of the θ rotation table 6, and the inspection beam 21 is set to the inner edge of the donut. After that, the work table 3 is moved in the radial (R) direction of the test subject 2, e.g. in the lateral direction in FIG. 1 using the rectilinear table 5, while the work table 3 is rotated at a constant speed using the θ rotation table 6. Thus, it is possible to scan the inspection beam 21 over the entire surface of the test subject 2. More specifically, it is possible to perform inspection.

Scanning may be performed in a rectangular manner, not limited to a helical manner, or the inspection optical system 1 may be moved for scanning.

The measured data of the scattered light at measured points in the case of scanning the entire surface is converted into digital values through the pre-processing unit 4 and forwarded to the data processing unit 11, and the (scanned) positions of measured points defined by the encoders 5a and 6a and measured values at these points are stored in a measured result recording area 13c of the storage unit 13. A defect analyzing program 13a stored in the storage unit 13 analyzes the data of the measured points at which the positions are recognized for allowing inspection of foreign substances or the like including the scratch S, and the result can be displayed on a display device 15. It is noted that 16 denotes a bus in FIG. 1.

According to the embodiments described above, it is possible to provide an optical surface defect inspection apparatus and an optical surface defect inspection method that can improve a signal-to-noise ratio according to a multi-segmented cell method, and can implement highly sensitive inspection without performing autofocus operations.

What is claimed is:

1. An optical surface defect inspection apparatus comprising:
   an irradiating unit configured to irradiate an inspection beam onto a test subject;
   a scattered light optical system configured to form an image of a scattered light from a surface of the test subject on a photo-detector; and
   a processing unit configured to inspect a defect on the surface of the test subject based on an output from the photo-detector, wherein:
   the photo-detector includes an optical fiber bundle having one end thereof forming a circular light receiving surface to receive the scattered light, and the other end thereof connected to a plurality of light receiving devices;
   the optical fiber bundle is divided into a plurality of fan-shaped cells in the light receiving surface, and connected to the light emitting devices in units of the fan-shaped cells;
   a number of the cells is an even number; and
   paired cells provided at positions opposite to each other are connected to a same light receiving device.

2. The optical surface defect inspection apparatus according to claim 1, wherein
   the processing unit determines that a scratch exists when at least a certain pair of the paired cells among the paired cells receive the scattered light with a significant value as compared with the other paired cells.

3. The optical surface defect inspection apparatus according to claim 1, wherein
the irradiating unit has a laser Light source.

4. The optical surface defect inspection apparatus according to claim 1, wherein:
the test subject is a disk-shaped magnetic disk or IC wafer; and
the apparatus comprising a scanning unit configured to two-dimensionally scan the inspection beam over the surface of the test subject.

5. An optical surface defect inspection method comprising:
irradiating an inspection beam onto a test subject;
forming an image of a scattered light from a surface of the test subject on a photo-detector; and
inspecting a defect on the surface of the test subject based on an output from the photo-detector, wherein:
the photo-detector includes an optical fiber bundle having one end thereof forming a circular light receiving surface to receive the scattered light, and the other end thereof connected to a plurality of light receiving devices;
the optical fiber bundle is divided into a plurality of fan-shaped cells in the light receiving surface, and connected to the light emitting devices in units of the fan-shaped cells for performing the inspection based on outputs of the plurality of cells;
a number of the cells is an even number; and
paired cells provided at positions opposite to each other are connected to a same light receiving device.

6. The optical surface defect inspection method according to claim 5, wherein
the inspection determines that a scratch exists when at least a certain pair of the paired cells among the paired cells receive the scattered light with a significant value as compared with the other paired cells.

7. The optical surface defect inspection method according to claim 5,
wherein the inspection determines that a point-like defect or foreign substance exists when there is no significant difference in a light receiving level of the scattered light between the plurality of cells.

8. The optical surface defect inspection method according to claim 5,
wherein the test subject is a disk-shaped magnetic disk or IC wafer; and
the inspection is performed by two-dimensionally scanning the inspection beam over the surface of the test subject.

* * * * *